(12) United States Patent
Swink

(10) Patent No.: US 8,037,965 B1
(45) Date of Patent: Oct. 18, 2011

(54) STETHOSCOPE EXPANDER ASSEMBLY AND METHODS OF USING SAME

(76) Inventor: Kerry Swink, Oklahoma City, OK (US)

( * ) Notice: Subject to any disclaimer, the term of this patent is extended or adjusted under 35 U.S.C. 154(b) by 0 days.

(21) Appl. No.: 12/897,342

(22) Filed: Oct. 4, 2010

(51) Int. Cl.
*A61B 7/02* (2006.01)
*A61B 7/04* (2006.01)
*H04R 25/00* (2006.01)

(52) U.S. Cl. ........... 181/131; 181/135; 181/137; 381/67

(58) Field of Classification Search ................ 181/131, 181/135, 137; 381/67
See application file for complete search history.

(56) References Cited

U.S. PATENT DOCUMENTS

| | | | | |
|---|---|---|---|---|
| 257,487 | A * | 5/1882 | Ford ............................. | 181/131 |
| 717,898 | A * | 1/1903 | McCully ...................... | 181/135 |
| 3,623,571 | A * | 11/1971 | French ......................... | 181/135 |
| 3,746,124 | A * | 7/1973 | Wilson et al. ................ | 181/131 |
| 4,149,610 | A * | 4/1979 | Saiya et al. .................. | 181/131 |
| 4,277,654 | A * | 7/1981 | Penning ....................... | 381/309 |
| 4,406,346 | A * | 9/1983 | Pope, Jr. ...................... | 181/131 |
| 4,569,413 | A * | 2/1986 | Allen ........................... | 181/131 |
| 4,706,777 | A * | 11/1987 | Baumberg .................... | 181/131 |
| 5,466,898 | A * | 11/1995 | Gilbert et al. ................ | 181/131 |
| 5,847,330 | A * | 12/1998 | Grosslight ................... | 181/131 |
| 6,595,316 | B2 * | 7/2003 | Cybulski et al. ............. | 181/131 |
| 7,866,437 | B2 * | 1/2011 | MacMackin ................. | 181/131 |
| 2005/0103563 | A1 * | 5/2005 | Lam et al. .................... | 181/131 |
| 2009/0321196 | A1 * | 12/2009 | Bilan ............................ | 188/166 |
| 2010/0307860 | A1 * | 12/2010 | Ellingson ..................... | 181/131 |

* cited by examiner

*Primary Examiner* — Elvin G Enad
*Assistant Examiner* — Christina Russell
(74) *Attorney, Agent, or Firm* — Hall Estill Law Firm

(57) ABSTRACT

A stethoscope expander assembly includes a first portion and a second portion. Each portion is provided with at least one arm, at least one leg, and at least one attachment member. The first portion of the stethoscope expander assembly includes a male member and a cover opposite the male member. The second portion of the stethoscope expander assembly includes a female member and a channel for receiving a tubing of a stethoscope. The first and second portions provide a slit for receiving a spring of the stethoscope. The first and second portions of the stethoscope expander assembly function to move the stethoscope expander assembly into an expanded position.

19 Claims, 4 Drawing Sheets

STETHOSCOPE EXPANDER ASSEMBLY AND METHODS OF USING SAME

CROSS-REFERENCE TO RELATED APPLICATION

Not applicable.

FIELD OF THE INVENTION

The present invention relates generally to stethoscopes, and more particularly, but not by way of limitation, to a stethoscope expander assembly for expanding at least one ear tube of a stethoscope so as to allow for the positioning of each earpiece in the ear of an individual using one hand.

BACKGROUND OF THE INVENTION

Stethoscopes have long been used by mechanics to monitor machinery or health care professionals, such as doctors, nurses, technicians, veterinarians, etc., to monitor sounds produced by the heart, lungs, abdomen, and other structures in both humans and animals to diagnose illnesses. Sounds within engines or the body cause the stethoscope's diaphragm to vibrate, resulting in acoustic waves that travel via air-filled tubes to earpieces placed into the user's ears. There are various types of stethoscopes, such as acoustic and electronic. A traditional acoustic stethoscope is typically composed of a sound receiver assembly with a diaphragm and resonance chamber, flexible single or dual lumen tubing, two ear tubes, and two earpieces.

Typically, health care professionals are often performing other tasks when using the stethoscope, such as palpating the patient's pulse, holding the patient's chart, or manipulating equipment like a sphygmomanometer or thermometer. The design of a traditional stethoscope requires two hands to pull apart the ear tubes for placement of the earpieces into each ear.

Veterinarians also use stethoscopes to detect internal sounds produced by pets, livestock, and other animals. Often, veterinarians must hold down or subdue an anxious and agitated animal while attempting to hear the animal's internal noises, or must displace an animal's leg or other body part to allow access to vital areas. Manually separating the two ear tubes of a traditional stethoscope to place the earpieces in each ear requires two hands.

Further, disease-causing microorganisms are widespread in health care environments. In these locations pathogenic microorganisms are frequently found on patients' skin and clothing as well as on other surfaces in such an environment. Manually separating the two ear tubes of a traditional stethoscope to place earpieces in each ear requires two hands which may touch the caregiver's face or neck, thus possibly transmitting microorganisms. While known devices are directed to preventing the transmission of microorganisms between patients and/or health care professionals, there remains a need for an inexpensive, effective and easily-operated means for inhibiting the transmission of microorganisms.

To this end, although stethoscopes of the existing art are operable, further improvements or additions are desirable to be provided to a stethoscope which functions to be operated with one hand to expand at least one ear tube of a stethoscope so as to allow the positioning of an earpiece in the ear of an individual using one hand. It is to such a stethoscope expander assembly that at least one embodiment of the present invention is directed.

DETAILED DESCRIPTION OF THE INVENTION

Figure 1:
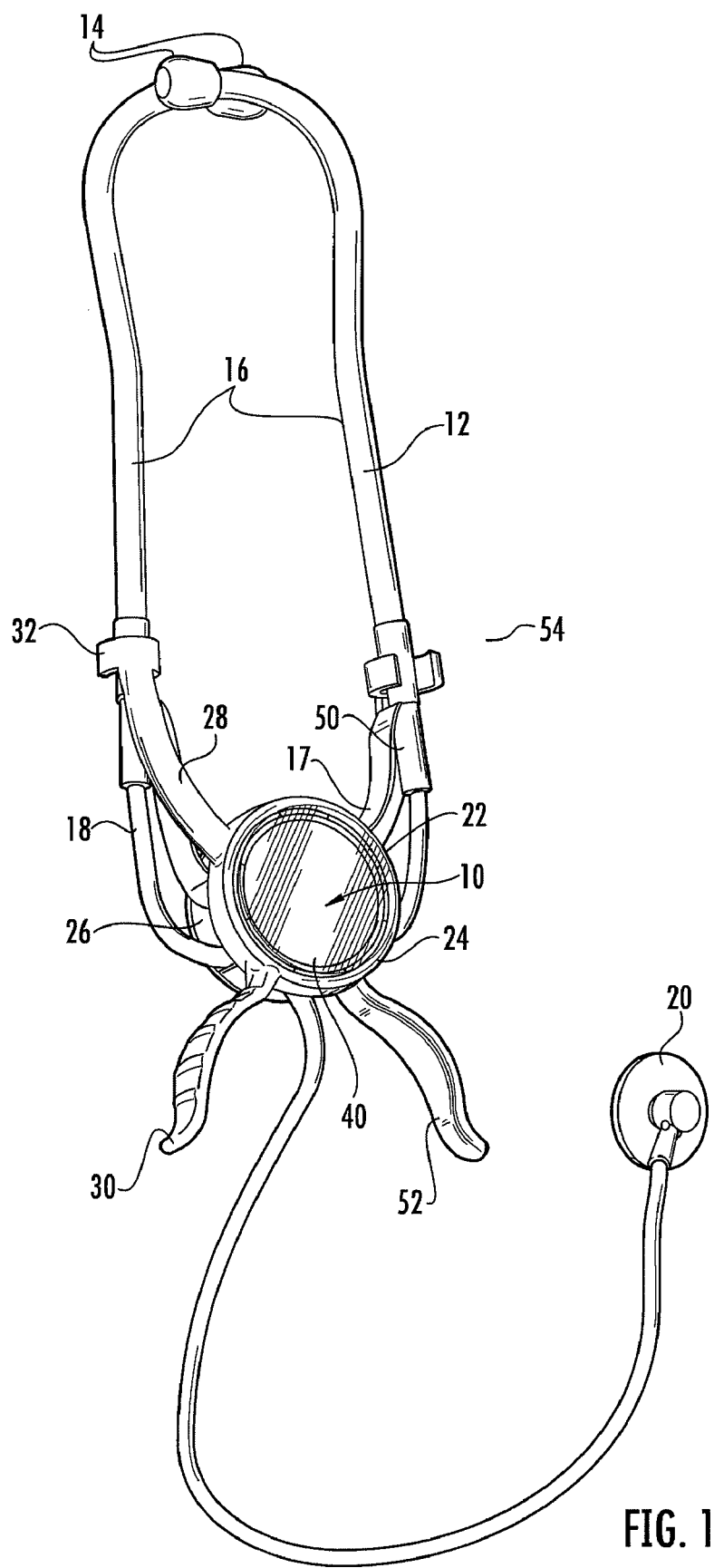
FIG. 1 is a perspective view of a stethoscope expander assembly constructed in accordance with the present invention, the stethoscope expander assembly being positioned on a portion of a stethoscope.

Referring now to the drawings, and more particularly to FIG. 1, shown therein is a stethoscope expander assembly 10 constructed in accordance with the present invention, the stethoscope expander assembly 10 being positioned on a portion of a stethoscope 12. The stethoscope 12 includes earpieces 14, ear tubes 16, a spring 17, tubing 18, and a chestpiece 20. The stethoscope 12 is shown in FIG. 1 as a dual lumen stethoscope. However, it should be understood by one of ordinary skill in the art that the stethoscope expander assembly 10 may be configured in any variety of ways to be positioned on a single tube or other style stethoscope such that the stethoscope expander assembly 10 may be used with a stethoscope having a spring, a tube and spring, a tube, or other configuration. Further, although the stethoscope 12 is shown having a single-sided chestpiece, it should be understood by one of ordinary skill in the art that the stethoscope expander assembly 10 may be utilized with a stethoscope having a double-sided or any other type of chestpiece. It should be understood by one of ordinary skill in the art that the stethoscope expander assembly 10 may be configured in any variety of ways to be utilized with any type of stethoscope, used for individuals, animals or machinery, so long as the stethoscope expander assembly 10 functions in accordance with the present invention as described herein.

It is contemplated, in one embodiment, that the stethoscope expander assembly 10 is constructed from two pieces of material, however, it should be understood that the stethoscope expander assembly 10 may be constructed from various components or from one solid piece of material. The stethoscope expander assembly 10 is preferably made of durable materials which are strong enough to allow movement of the stethoscope expander assembly 10. The stethoscope expander assembly 10 may be constructed from a variety of durable and resilient materials, such as for example, polymeric materials, plastics, thermoplastics, elastomers, rubber, cardboard, metals such as aluminum, steel, titanium, magnesium or alloys containing these metals, and composite materials which are capable of providing the desired strength and durability for the stethoscope expander assembly 10. Further, it should be understood that the stethoscope expander assembly 10 may be constructed from materials that may be water-resistant, anti-microbial, or waterproof so that the stethoscope expander assembly 10 may be easily cleaned and/or disinfected after use.

In addition, the stethoscope expander assembly 10 may be constructed from any disposable material, such as a disposable waxed or coated flexible paper or thin plastic. The stethoscope expander assembly 10 may also be constructed in any of a variety of colors and patterns. Further, it will be appreciated that the stethoscope expander assembly 10 can be sized and shaped from any suitable material, that is completely or partially positioned on or about the stethoscope or a portion of the stethoscope. A clip may be provided to a portion of the stethoscope expander assembly 10 for attaching to a belt or bag of an individual.

Figure 2:
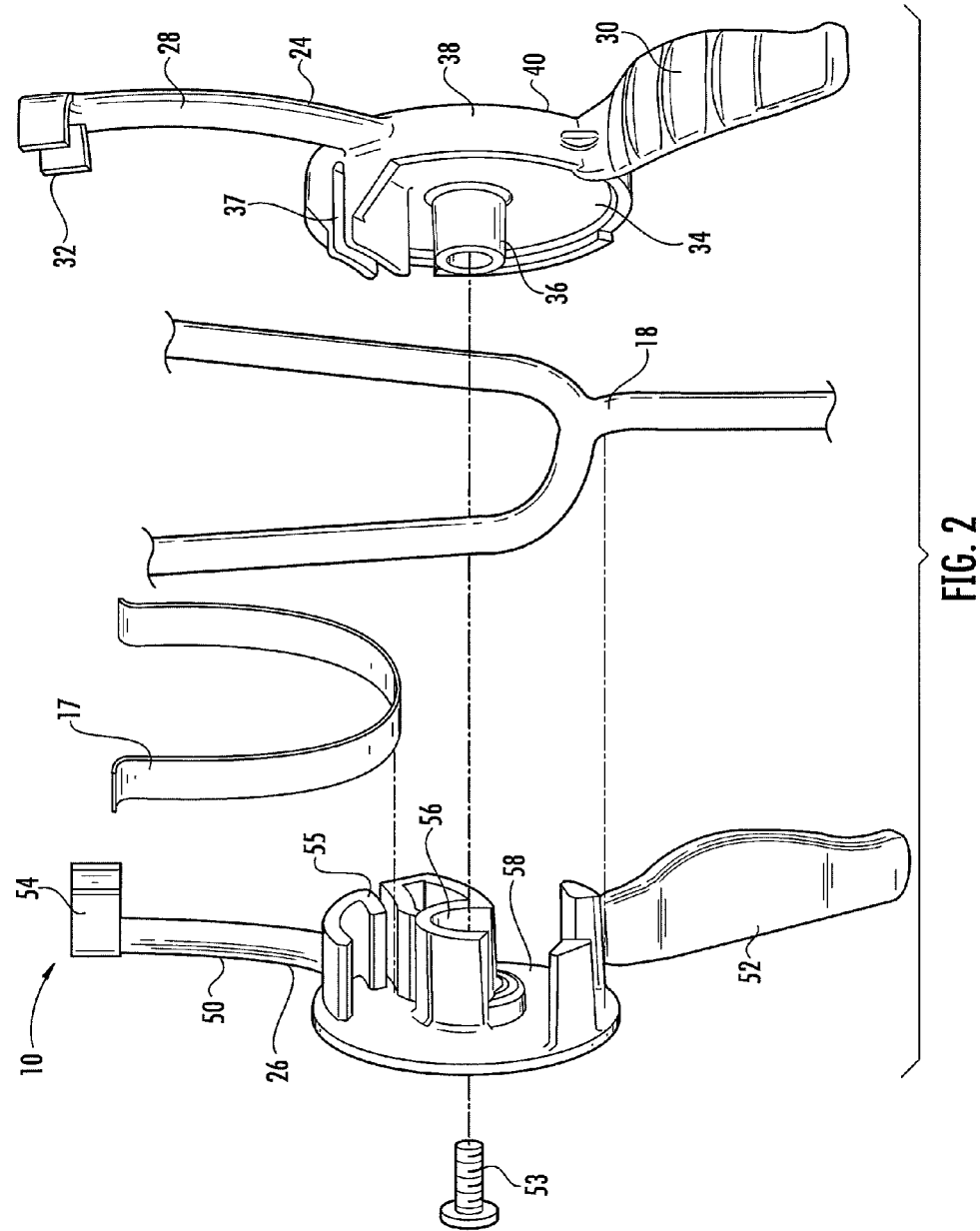
FIG. 2 is a perspective view of a first portion and a second portion of the stethoscope expander assembly of FIG. 1.

Referring to FIGS. 1-2, in one embodiment, the stethoscope expander assembly 10 includes a body 22 having a first portion 24 and a second portion 26. The first portion 24 is provided with a first arm 28 and a first leg 30. The first arm 28 and the first leg 30 are shown positioned on an adjacent side of the first portion 24. However, it should be understood that the first arm 28 and the first leg 30 may be configured to be positioned on opposing sides so long as the stethoscope expander assembly 10 functions in accordance with the present invention described herein.

The first arm 28 includes an attachment member 32 for detachably connecting the first arm 28 about at least a portion of the ear tube 16 of the stethoscope 12. The attachment member 32 may be any such fastener known in the art for fastening or removable securing one object to another including, for example, snaps, zip locks, Velcro-type fasteners, and adhesive substances. It should be understood that any number and configurations of arms, legs, and attachment members may be provided to the first portion 24 of the stethoscope expander assembly 10 so long as the arms, legs and attachment members function in accordance with the present invention as described herein. Further, it should be understood by one of ordinary skill in the art that although the first arm 28 is shown positioned on the ear tube 16 of the stethoscope, the first arm 28 of the stethoscope expander assembly 10 may be positioned on any portion of the stethoscope 12 so long as the stethoscope expander assembly 10 functions in accordance with the present invention.

A first surface 34 of the first portion 24 is provided with at least one male connector member 36 and a slit portion 37. At least one male connector member 36 may be adapted to receive a suitable fastener, such as a pin, screw, bolt, and combinations thereof. A second surface 38 of the first portion 24 is provided with a cover 40. The cover 40 may be provided for a variety of images, letters, characters, words, symbols, or pictures. Such images can be used to communicate text or images to a patient. In some embodiments, the text may refer to products and companies for advertising purposes; images may depict products or company logos. In another embodiment, an image may be configured to depict a cute animal or character. An image may affect or influence the patient towards a more positive demeanor by distracting the patient during an examination. The image may evoke feelings of joy, happiness and laughter, especially for children.

The first portion 24 is shown as substantially circular in shape, however, it should be understood that the first portion 24 may be any shape, such as oval, square, rectangular, triangular, polygonal, quadrilateral, ellipsoidal and the like, for example.

The second portion 26 of the stethoscope expander assembly 10 is provided with a second arm 50 and a second leg 52. The second arm 50 and the second leg 52 are shown positioned on an adjacent side of the second portion 26. However, it should be understood that the second arm 50 and the second leg 52 may be configured to be positioned on opposing sides so long as the stethoscope expander assembly 10 functions in accordance with the present invention described herein. Further, it should be understood that the first arm 28, first leg 30, second arm 50, and second leg 52 may be positioned in various configurations and positions about the first portion 24 and the second portion 26 so long as the stethoscope expander assembly 10 functions in accordance with the present invention as described herein.

The second arm 50 includes an attachment member 54 for detachably connecting the second arm 50 about at least a portion of the ear tube 16 of the stethoscope 12. The attachment member 54 may be any such fastener known in the art for fastening or removable securing one object to another including, for example, snaps, zip locks, Velcro-type fasteners, screws, clamps, and adhesive substances. It should be understood that any number and configurations of arms, legs, and attachment members may be provided to the second portion 26 of the stethoscope expander assembly 10 so long as the arms, legs and attachment members function in accordance with the present invention as described herein. Further, it should be understood by one of ordinary skill in the art that although the second arm 50 is shown positioned on the tubing 18 of the stethoscope, the second arm 50 of the stethoscope expander assembly 10 may be positioned on any portion of the stethoscope 12 so long as the stethoscope expander assembly 10 functions in accordance with the present invention.

The second portion 26 is provided with at least one opening 56 or female member for matingly receiving at least one male connector member 36 such that the first portion 24 is pivotally connected to the second portion 26. At least one opening 56 may be completely or partially closed and may be adapted to receive a suitable fastener 53, such as a pin, screw, bolt, and combinations thereof. At least one male connector member 36 and at least one opening 56 may be configured so that the first portion 24 and the second portion 26 are connected to one another in a floating arrangement.

The second portion 26 is provided with a slit portion 55 such that when the first portion 24 and the second portion 26 are connected, the slit portion 37 and the slit portion 55 form a slit 57 for receiving the spring 17, if included in the stethoscope.

A channel 58 is formed in the second portion 26. The channel 58 is sized and dimensioned for receiving the tubing 18 of the stethoscope 12. The channel 58 may be configured in various sizes and dimensions for receiving various portions of the stethoscope 12. In another embodiment, the channel 58 may be configured to snap fit to a portion of a stethoscope.

The tubing 18 of the stethoscope 12 is positioned in the channel 58 of the second portion 26. The male connector member 36 of the first portion 24 is disposed in the opening 56 such that the first portion 24 is positioned about the second portion 26 of the stethoscope expander assembly 10. Upon matingly disposing the male connector member 36 in the opening 56, the first portion 24 and the second portion 26 may be pivotally connected to form the body 22. It should be understood to one of ordinary skill in the art that the first portion 24 and the second portion 26 may be configured to be movably connected to one another in various ways, so long as the stethoscope expander assembly 10 functions in accordance with the present invention. The first portion 24 and the second portion 26 may be fastened to one another with any suitable fastener, including screws, pins, bolts, brackets and combinations thereof. The attachment members 32 and 54 are detachably connected to opposing ear tubes 16 or opposing portions of tubing 18 of the stethoscope 12.

Figure 3:
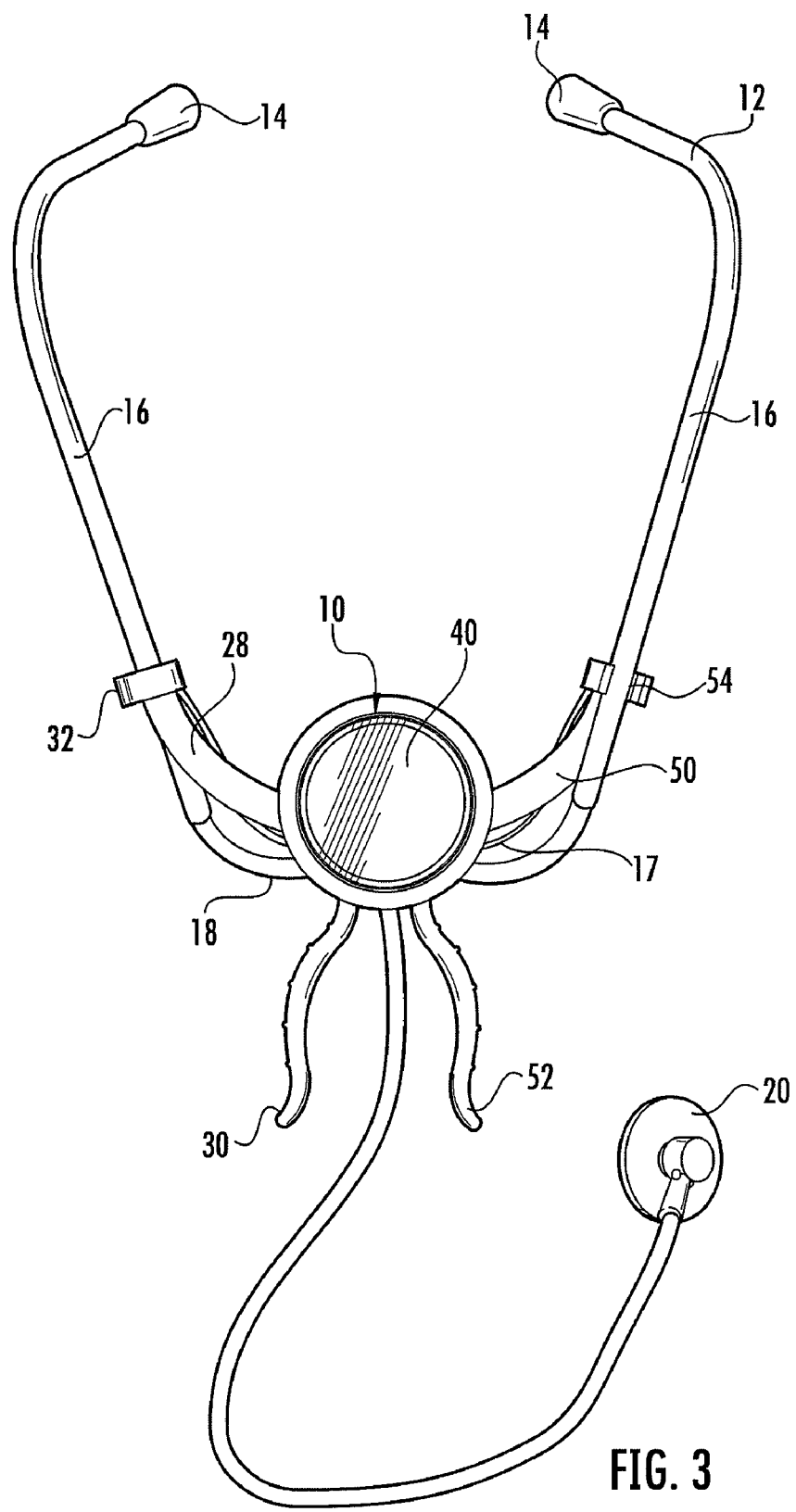
FIG. 3 is a perspective view of the stethoscope expander assembly of FIG. 1 positioned on the stethoscope in an expanded position.
Figure 4:
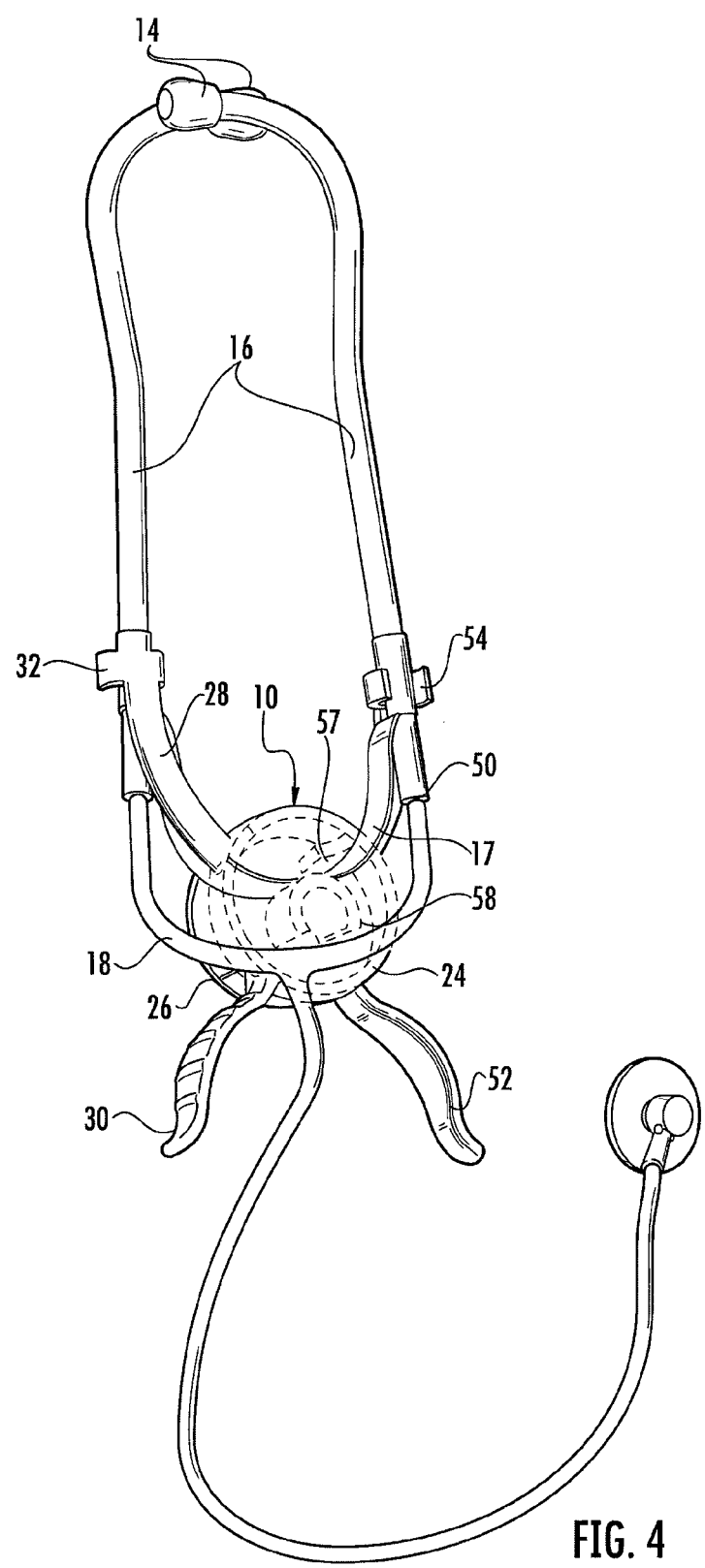
FIG. 4 is a perspective view of the stethoscope expander assembly of FIG. 1 positioned on the stethoscope in a closed position.

Referring to FIGS. 3 and 4, the stethoscope expander assembly 10 is movable between an expanded position (FIG. 3) and a closed position (FIG. 4). In the expanded position, the first leg 30 of the first portion 24 and the second leg 52 of the second portion 26 are pivotally moved in a first direction toward each other such that the first arm 28, detachably connected to an ear tube 16, and the second arm 50, detachably connected to an opposing ear tube 16, move away from each other.

In the closed position, the first leg 30 of the first portion 24 and the second leg 52 of the second portion 26 are pivotally moved in a second direction away from each other such that the first arm 28, detachably connected to an ear tube 16, and the second arm 50, detachably connected to an opposing ear tube 16, move toward each other. The first arm 28 and the second arm 50 apply pressure to the tubing 18 of the stethoscope 12 to maintain the stethoscope expander 10 assembly in the closed position.

In use, during the examination of a patient, a health care provider having a stethoscope 12 hanging from his/her neck grasps the stethoscope expander assembly 10 with one hand and removes the stethoscope 12 from about the health care provider's neck. The health care provider squeezes or provides a force to the first and second legs 30 and 52 so that the first and second arms 28 and 50 move apart, thus opening/expanding the ear tubes 16 of the stethoscope 12 a distance such that each ear piece 14 may be positioned into the ears of the health care provider.

Once the health care provider has completed the examination and the use of the stethoscope 12, the health care provider provides a force to the first and second legs 30 and 52, respectively, of the stethoscope expander assembly 10 with one hand, so that the first and second arms 28 and 50, respectively, move apart, thus opening/expanding the ear tubes 16 of the stethoscope 12 a distance such that each ear piece 14 may be removed from the ears of the health care provider. Once the ear pieces are removed, the health care provider releases the grasp of the first and second legs 30 and 52, respectively, and the resistant force of the spring or other mechanism moves the one ear tube 16 toward the other ear tube 16 so that the stethoscope expander assembly 10 is in the closed position and such that the stethoscope 12 is placed back around the neck of the health care provider. In another embodiment, the first leg 30 is manually moved away from the second leg 52 so that the stethoscope expander assembly 10 is in the closed position.

While the description above refers to particular embodiments of the present invention, it will be understood that many modifications may be made without departing from the spirit thereof. The claims are intended to cover such modifications as would fall within the true scope and spirit of the present invention. The presently disclosed embodiments are therefore to be considered in all respects as illustrative and not restrictive, the scope of the invention being indicated by the claims rather than the foregoing description, and all changes which come within the meaning and range of equivalency of the claims are therefore intended to be embraced therein.

What is claimed is:

1. A stethoscope expander assembly, comprising:
a first portion having at least one arm detachably connected to a portion of a stethoscope and at least one leg for moving the stethoscope expander assembly into an expanded position, wherein the first portion is provided with a male connector member; and
a second portion provided with an opening for matingly receiving the male connector member so as to movably connect the first portion and the second portion, the second portion having at least one arm detachably connected to a portion of the stethoscope and at least one leg for moving the stethoscope expander assembly into an expanded position, wherein when the stethoscope expander assembly is positioned in the expanded position, at least one ear piece of a stethoscope is positionable in at least one ear of an individual.

2. The stethoscope expander assembly of claim 1 wherein the second portion is provided with a channel for receiving a portion of tubing of the stethoscope for detachably connecting the stethoscope expander assembly to the stethoscope.

3. The stethoscope expander assembly of claim 1 wherein the first portion is provided with a channel for receiving a portion of tubing of the stethoscope for detachably connecting the stethoscope expander assembly to the stethoscope.

4. The stethoscope expander assembly of claim 1 wherein at least one arm of the first portion and at least one arm of the second portion are provided with an attachment member for detachably connecting to a portion of the stethoscope.

5. The stethoscope expander assembly of claim 4 wherein the attachment member is detachably connected substantially about an ear tube of the stethoscope.

6. The stethoscope expander assembly of claim 1 wherein the first portion includes a slit portion for receiving a spring of the stethoscope.

7. The stethoscope expander assembly of claim 1 wherein the second portion includes a slit portion for receiving a spring of the stethoscope.

8. The stethoscope expander assembly of claim 1 wherein the first portion and the second portion of the stethoscope expander assembly are pivotally connected so that the first portion and the second portion are movable in a first direction and a second direction wherein in the first direction, at least one arm of the first and second portions move toward each other and at least one leg of the first and second portions move away from each other and wherein in the second direction, at least one arm of the first and second portions move away from each other and at least one leg of the first and second portions move toward each other.

9. The stethoscope expander assembly of claim 1 wherein the first portion includes a cover for providing a text or image.

10. The stethoscope expander assembly of claim 1 wherein the first and second portions are configured to be removably connected with a fastener.

11. A method for expanding at least one ear tube of a stethoscope so as to position an earpiece of the stethoscope in the ear of an individual, comprising the steps of:
providing a stethoscope expander assembly, the stethoscope expander assembly, comprising:
a first portion having at least one arm detachably connected to a portion of a stethoscope and at least one leg for moving the stethoscope expander assembly into an expanded position, wherein the first portion is provided with a male connector member; and
a second portion provided with an opening for matingly receiving the male connector member so that the second portion is movably connected to the first portion, the second portion having at least one arm detachably connected to a portion of the stethoscope and at least one leg for moving the stethoscope expander assembly into an expanded position;
detachably connecting the stethoscope expander assembly to a portion of the stethoscope; and
positioning the stethoscope expander assembly in the expanded position, wherein at least one ear piece of a stethoscope is positionable in at least one ear of an individual.

12. The method of claim 11, further comprising the step of: removing at least one ear piece of the stethoscope from at least one ear of the individual.

13. The method of claim 11, wherein the first portion and the second portion of the stethoscope expander assembly are pivotally connected so that the first portion and the second portion are movable in a first direction and a second direction wherein in the first direction, at least one arm of the first and second portions move toward each other and at least one leg of the first and second portions move away from each other and wherein in the second direction, at least one arm of the first and second portions move away from each other and at least one leg of the first and second portions move toward each other.

14. A stethoscope expander assembly, comprising:
   a first portion having at least one arm detachably connected to at least one ear tube of a stethoscope and at least one leg for moving the stethoscope expander assembly into an expanded position, the first portion having a male connector member; and
   a second portion having an opening for matingly receiving the male connector member of the first portion so that the second portion is pivotally connected to the first portion, the second portion having at least one arm detachably connected to at least one ear tube of the stethoscope and at least one leg for moving the stethoscope expander assembly into an expanded position, wherein when the stethoscope expander assembly is positioned in the expanded position, at least one ear piece of a stethoscope is positionable in at least one ear of an individual.

15. The stethoscope expander assembly of claim 14 wherein the second portion is provided with a channel for receiving a portion of tubing of the stethoscope for detachably connecting the stethoscope expander assembly to the stethoscope.

16. The stethoscope expander assembly of claim 14 wherein the first portion includes a slit portion for receiving a spring of the stethoscope.

17. The stethoscope expander assembly of claim 14 wherein the first portion and the second portion of the stethoscope expander assembly are pivotally connected so that the first portion and the second portion are movable in a first direction and a second direction wherein in the first direction, at least one arm of the first and second portions move toward each other and at least one leg of the first and second portions move away from each other and wherein in the second direction, at least one arm of the first and second portions move away from each other and at least one leg of the first and second portions move toward each other.

18. The stethoscope expander assembly of claim 14 wherein the first portion includes a cover for providing a text or image.

19. The stethoscope expander assembly of claim 14 wherein the first and second portions are configured to be removably connected with a fastener.

* * * * *